United States Patent
Andreasson et al.

(10) Patent No.: US 9,681,669 B2
(45) Date of Patent: Jun. 20, 2017

(54) **PLANT EXTRACTS COMPRISING AT LEAST A PHENOLIC COMPOUND, FOR INDUCING THE NATURAL DEFENSE OF A PLANT AGAINST A PATHOGEN, SUCH AS *PHYTOPHTHORA INFESTANS***

(71) Applicants: Erik Andreasson, Eslöv (SE); Marit Lenman, Lund (SE)

(72) Inventors: Erik Andreasson, Eslöv (SE); Marit Lenman, Lund (SE); Laith Moushib, Malmo (SE)

(73) Assignees: Erik Andreasson, Eslov (SE); Marit Lenman, Lund (SE)

( * ) Notice: Subject to any disclaimer, the term of this patent is extended or adjusted under 35 U.S.C. 154(b) by 0 days.

(21) Appl. No.: 14/426,837

(22) PCT Filed: Sep. 10, 2013

(86) PCT No.: PCT/SE2013/051052
§ 371 (c)(1),
(2) Date: Mar. 9, 2015

(87) PCT Pub. No.: WO2014/042578
PCT Pub. Date: Mar. 20, 2014

(65) Prior Publication Data
US 2015/0245620 A1    Sep. 3, 2015

(30) Foreign Application Priority Data

Sep. 11, 2012  (SE) ...................... 1251015

(51) Int. Cl.
| | |
|---|---|
| *A01N 65/08* | (2009.01) |
| *A01N 37/40* | (2006.01) |
| *A01N 43/16* | (2006.01) |
| *C13B 20/06* | (2011.01) |
| *C05G 3/00* | (2006.01) |
| *C05D 9/02* | (2006.01) |
| *C05F 11/10* | (2006.01) |

(52) U.S. Cl.
CPC ............ *A01N 65/08* (2013.01); *A01N 37/40* (2013.01); *A01N 43/16* (2013.01); *C05D 9/02* (2013.01); *C05G 3/00* (2013.01); *C13B 20/06* (2013.01); *Y02E 50/343* (2013.01); *Y02W 30/47* (2015.05)

(58) Field of Classification Search
CPC ........ A01N 37/40; A01N 43/16; A01N 65/08; C05D 9/02; C05F 11/10; C05G 3/00; C05G 3/02; C13B 20/06; Y02E 50/343; Y02W 30/47
See application file for complete search history.

(56) References Cited

U.S. PATENT DOCUMENTS 3,734,773 A    5/1973 Haley

OTHER PUBLICATIONS

Mosen Asadi, Chapter 5: Sugarbeet Processing—Section 11: Sedimentation and Filtration; Beet-Sugar Handbook, Wiley-Interscience, p. 269 (Jan. 1, 2007).
Official Action from corresponding European Application No. 13836494.8, dated Apr. 7, 2016.
Moushib, "Sugar beet extract induces defence against Phytophthora infestans in potato plants", European Journal of Pathology, Jun. 2013, vol. 136, nr 2, p. 261-271.
Godshall et al., "Phenolics in sugar products: their role in flavor and color production", Proceedings of the Sugar Processing Research Conference (1983), p. 47-72.
Massart, Inhibiteurs de la Germination Dans Les Glomerules de la Betterave a Sucre et Dans D'Autres Fruits Secs ET Graines, Biochimia, vol. 22, No. 1-2, 1957, p. 417-420. With English translation of Summary and Conclusions.
Wettasinghe et al., "Phase II enzyme inducing and antioxidant activities of beetroot (*Beta vulgaris* L.) Extracts from phonotypes of different pigmentation", Journal of Agricultural and Food Chemistry, 2002, vol. 50, p. 6704-6709.
Indhumathi, "Hematopoietic study of the methanolic root extract of Beta vulgaris on albino rats—an in vivo study", Int J Pharm Bio Sci Oct. 2012; 3(4):(B), p. 1005-1015.
Loginova, "Quality and filtration characteristics of sugar beet juice obtained by "cold" extraction assisted by pulsed electric field", Journal of Food Engineering, 106, (2011), p. 144-151.
Sebeson, "Gallic acid in sugarbeet fruits", Journal of the American Society of Sugar Beet Technologist, vol. 15, Oct. 1969, p. 617-624.
Liljeroth, "Induced resistance in potato to Phytophthora infestans-effect of BABA in greenhouse and field tests with different potato varieties", EUR J Plant Pathol., (2010) 127:127-183.
Widmer et al., "Plant extracts containing caffeic acid and rosmarinic acid inhibit zoospore germination of *Phytophthora* spp. Pathogenic to Theobroma cacao", European J of Plant Pathology, (2006), 115: 377-388.

(Continued)

*Primary Examiner* — John Pak
*Assistant Examiner* — Nathan W Schlientz
(74) *Attorney, Agent, or Firm* — Porter Wright Morris & Arthur LLP (57) ABSTRACT

A sugar beet extract (SBE) induced defense in potato plants under green-house conditions and in field trial, without apparent toxicity for the plant. Treatment with SBE resulted in significant reduction of the size of *Phytophthora infestans* infection lesions and lower sporangia production. SBE had no apparent toxic effect, neither on the hyphal growth of the pathogennor on the germination of sporangia. SBE triggered PR-1 protein induction which suggests that the defense mechanism conferred by SBE could be via direct induced resistance. An array of phenolic metabolites and minerals was found in the SBE and constitutes potential inducers of the defense.

27 Claims, 7 Drawing Sheets

(56) References Cited

OTHER PUBLICATIONS

Gennari et al., "Total Extract of *Beta vugaris* Var. *cicla* Seeds versus Its Purified Phenolic Components: Antioxidant Activities and Antiproliferative Effects Against Colon Cancer Cells", Phytochem. Anal., (2011) 22, 272-279.

Coquoz et al., Arachidonic Acid Induces Local but not Systemic Synthesis of Salicylic Acid and Confers Systemic Resistance in Potato Plants to Phytophthora infestans and Alternaria solani, Phytopathology, vol. 85, No. 10, (1995), p. 1219.

Sebeson et. al., Gallic Acid in Sugarbeet Fruits, Journal of the American Society of Sugar Beet Technologist, 15(7):617-624, XP055189588 (Oct. 1969).

Official Action from corresponding European Application No. 13836494.8, dated Jan. 9, 2017.

PLANT EXTRACTS COMPRISING AT LEAST A PHENOLIC COMPOUND, FOR INDUCING THE NATURAL DEFENSE OF A PLANT AGAINST A PATHOGEN, SUCH AS *PHYTOPHTHORA INFESTANS*

TECHNICAL FIELD

The present embodiments relate to a plant extract and its use in protecting plants from pathogenic attacks. In particular, the present embodiments relate to a plant extract, which, upon application to a plant or crop, helps protecting the plant or crop against an infection without being directly toxic to the pathogen causing the infection.

BACKGROUND

Although plant disease management policies are continuously developed all over the world, modern agriculture still faces devastating plant diseases. One of the most important diseases is potato late blight caused by the oomycete *Phytophthora infestans* that cause billion-dollar losses annually. The current control strategies of the disease are mainly fungicide application and breeding of cultivars with dominant resistance genes. The pathogen is notorious for its ability to overcome resistance and this is why many control strategies need always to be explored.

The prior art teaches a wide variety of materials that protect plants. Natural antimicrobial metabolites from plants having an effect on the growth of the phytopathogens have been used. Suppression of late blight development on tomato plants was achieved with ethanolic plant extracts of *Paeonia suffruticosa* and *Hedera helix*, both of which inhibited *P. infestans* zoospore release and germination (Röhner et al. 2004). Plant extracts of *Rheum rhabarbarum* and *Solidago canadensis* reduced the growth of *P. infestans* on potato leaves by directly inhibiting *P. infestans* growth (Stephan et al. 2005). Antibacterial, antifungal, and anti-oomycete activity of garlic juice has been reported and found to reduce the severity of late blight disease in potato plants (Slusarenko et al. 2008). A commercial product which shows an efficacy against *P. infestans* on potatoes is Elot-Vis®, which is based on an ethanolic plant extract (Stephan et al. 2005). Elot-Vis® showed effect against *P. infestans* on potato crops but only reduced disease if applied one day before *P. infestans* inoculation (Stephan et al. 2005). Elot-Vis® is directly toxic to the pathogen (Stephan et al. 2005).

Promising results achieved with the application of some plant defense inducing agents suggest that the principle of induced resistance might be employed in integrated disease management programs.

Resistance against *P. infestans* has been linked to the effect of a number of phenolic compounds like chlorogenic acid, p-coumaric acid, ferulic acid, rosmarinic acid, salicylic acid, 4-hydroxybenzaldehyde, and 4-hydroxybenzoate (Coquoz et al. 1995; Widmer and Laurent 2006). The commonly reported functions of phenolic compounds in the literature have been assigned to two main functions. Phenolic compounds can either have a direct toxic (antimicrobial) effect on the pathogens, e.g. soluble phenolic acids, or they can induce a barrier against pathogens by strengthening the cell wall to make it more resistant to the cell-wall degrading enzymes, e.g. cell wall-bound phenolics.

SUMMARY

It is an objective to provide a natural agent that can induce defense in plants against biotic stress.

It is a particular objective to provide such an agent that can be used to combat plant pathogens, in particular *Phytophthora infestans* causing late blight disease.

These and other objectives are met by embodiments as disclosed herein.

An aspect of the embodiments relates to a plant extract comprising at least one phenolic compound and obtainable from a solid fraction of carbonated sugar beet root juice.

In a particular, but optional embodiment, the plant extract is obtained by extraction, using a solvent, from the solid fraction of carbonated sugar beet root juice.

In another particular, but optional embodiment, the plant extract comprises p-hydroxybenzoic acid at a concentration of more than 5 μg/ml, preferably at least 10 μg/ml.

In a further particular, but optional embodiment, the plant extract protects a plant against an infection of a pathogen but is not toxic to the pathogen at a working concentration adapted to be applied to the plant.

Another aspect of the embodiments relates to a composition comprising the plant extract as mentioned above and at least one plant signaling agent and/or fungicide.

Further aspects of the embodiments relate to a method of inducing resistance to biotic stress in a plant and a method of treating, inhibiting or reducing late blight disease in a plant. These methods comprise applying a plant extract and/or composition as mentioned above to the plant.

Still another aspect of the embodiments relates to a method of manufacturing a plant extract comprising at least one phenolic compound. The method comprises mixing a solvent with a solid fraction of carbonated sugar beet root juice. The mixture is allowed to settle to form a supernatant and settled solids. The supernatant is separated from the settled solids and used to produce the plant extract.

The present embodiments provide an immunoboosting plant extract that is capable of inducing the natural defense of a plant against infections of a pathogen. The plant extract is able to achieve this protecting effect in plants without being toxic per se to the pathogen at the concentrations to be used for treating the plant.

BRIEF DESCRIPTION OF THE DRAWINGS

The embodiments, together with further objects and advantages thereof, may best be understood by making reference to the following description taken together with the accompanying drawings, in which:

FIGS. 1b-1d illustrate lesion size measurements 6 days post infection (6 dpi) for potato plants. Leaves were from Desiree (FIG. 1b), Bintje (FIG. 1c), and Ovatio (FIG. 1d). Data show mean values of lesion measurements in mm from two combined experiments for each genotype and the error bars represent the standard error of the mean of the two combined experiments each performed with 12 leaves. Different letters represent data that are statistically different from each other according to Tukey's multiple range test ($P<0.05$).

FIG. 2 illustrates sporangia production 10 days post infection (10 dpi) in Desiree. Leaves from Desiree plants treated with water, SBE, and BABA (0.3 g/l) were taken and inoculated with *P. infestans* (15 000 sporangia/ml) in a detached leaf assay. Data show mean values of sporangia concentration from two combined experiments and the error bars represent the standard error of the mean of the two combined experiments each performed with 12 leaves. Different letters represent data that are statistically different from each other according to Tukey's multiple range test ($P<0.05$).

FIG. 3*a* illustrates the direct effect of SBE on the hyphal growth of the pathogen *P. infestans*. Seven days after growing *P. infestans* on pea agar, sterile paper discs (12 mm diameter) were placed 5 mm outside the opposite edges of a hyphal colony of *P. infestans* growing on pea agar medium. Paper discs were impregnated with 80 μl water (A) or SBE (B). Two to three days later, the hyphal growth surrounding the sites of the impregnated paper discs was inspected.

FIG. 3*b* illustrates the percentage of sporangia germination as revealed by the microscopic examination of the sporangial solution. Percentage of germinated sporangia was estimated in four randomly chosen microscopic fields from samples treated with 1% ethanol (EtOH) and SBE one day after incubating the samples in the incubator in the dark at 21° C. The experiment was done in a total volume of 1 ml (in Eppendorf tubes) using three replicates. The sporangia concentration was 40 000 sporangia/ml and the final concentration of SBE was 20% and for EtOH it was 1%. Data show mean percentage of sporangia germination from two combined experiments and the error bars represent the standard error of the mean of the two combined experiments each performed with three replicates for each treatment.

FIG. 4 illustrates SDS-PAGE analysis of the apoplastic proteins in potato leaves. Apoplastic fluids from leaves of the three different potato genotypes treated with water, BABA (0.3 g/l), and SBE were analyzed for PR-1 protein induction. From left to right M: Molecular size marker; DC: Desiree Control (water); DB: Desiree BABA (0.3 g/L); DE: Desiree Extract (SBE); OC: Ovatio Control; OB: Ovatio BABA; OE: Ovatio Extract (SBE); BC: Bintje Control; BB: Bintje BABA; BE: Bintje Extract (SBE). 30 μl from each sample, which equals one sixth of the total apoplastic fluid extracted from each sample, were loaded into each well.

FIG. 5 illustrates HPLC profile of SBE at 280 nm and examples of UV-spectra for the detected phenolic compounds (numbers above the peaks correspond to numbers by the UV-spectra scanned at wavelength range 200 to 400 nm). Peak 1: p hydroxybenzoic acid; peak 2: vanillic acid; peak 3: epicatechin gallate; peak 4: isoferulic acid; peak 6: cinnamic acid.

FIG. 6 illustrates field experiment with control plants (C) and plants sprayed three times with one week interval using 20% sugar beet extract (SBE). Bintje plants were sprayed with 20% SBE for another three times with one week interval. Given are percentages of infected leaves 11 days after infection in Bintje and Ovatio.

FIGS. 7A and 7B illustrate HPLC chromatograms, absorbance at 280 nm, of sugar beet extract (SBE) (FIG. 7A) and Speedi-Beet extract (FIG. 7B).

DETAILED DESCRIPTION

The present embodiments generally relate to a plant extract that can be used as biopesticide for defense against biotic stresses, such as various plant pathogens. The plant extract of the embodiments can therefore be used to stimulate the defenses of a plant by inducing its resistance to such biotic stresses. The plant extract can also be used to prevent or treat, or at least inhibit or alleviate, plant diseases such as late blight disease.

The plant extract of the embodiments can be regarded as an immunoboosting composition that is able to induce a defense against biotic stresses, such as various plant pathogens, in plants. The plant extract is able to perform this beneficial effect without being toxic to the plant pathogen at the working concentrations that are used to treat the plant. Thus, the plant extract itself, when applied to the plant pathogens, will not be toxic to the plant pathogen but is still able to, when applied to a plant, protect the plant from infection of the plant pathogen by inducing and promoting the natural defense of the plant against the pathogens.

The plant extract of the embodiments is a phenolic-containing plant extract obtained from sugar beet (*Beta vulgaris*). The plant extract therefore comprises at least one phenolic compound but typically a mixture of various phenolic compounds.

The plant extract can be obtained from sugar beet root as raw material and/or from a processed sugar beet root product. Such a processed sugar beet root product is a processed form of sugar beet root, such as a byproduct or waste product, typically obtained during sugar production from the sugar beet roots.

A typical such sugar production process involves washing the sugar beet roots and slicing, typically mechanically slicing, them into thin strips traditionally called cossettes. These cossettes are then passed to a so called diffuser, which is a machine that extracts the sugar content into a water solution called the raw juice.

The used cossettes, or pulp, exit the diffuser at a high water content (about 95% moisture) but low sucrose content. This wet pulp may then be pressed, such as in a screw press to a reduced moisture content, such as about 65-75% moisture, and optionally dried to an even lower moisture content. The dried pulp is a byproduct traditionally used as animal feed.

The raw juice is subject to a carbonation process which removes impurities from the raw juice prior to crystallization. In a typical approach, the raw juice is mixed with hot milk of lime (a suspension of calcium hydroxide in water). This treatment precipitates a number of impurities as their calcium salts and large organic molecules aggregate in the presence of the multivalent calcium cations.

Carbon dioxide is then typically bubbled through the alkaline sugar solution, precipitating the lime as calcium carbonate (chalk). The formed chalk particles entrap some impurities and absorb others. The chalk particles with the impurities flocculate and thereby settle in the bottom of the clarifier or tank. An optional final addition of more carbon dioxide precipitates more calcium from the solution. After filtering off the solids, a golden light-brown sugar solution called thin juice remains. This thin juice is further processed, such as by pH modification, sulphitation and concentration, prior to crystallization to form sugar. The solid fraction obtained from this carbonation process is a byproduct traditionally used as fertilizer.

The processed sugar beet root product of the embodiments can be any processed product or byproduct obtained from the sugar beet root during sugar production. In a typically example the solid fraction obtained from the carbonation process could be used as the processed sugar beet root product of the embodiments. This solid fraction is then the remaining material following removal of the thin juice in the clarifier or tank.

Alternatively, the processed sugar beet root product is the used cossettes, i.e. the pulp, exiting the diffuser. The processed product can then be the wet pulp having a high moisture content, the pressed wet pulp having a lower moisture content, such as about 65-75% moisture or such a pressed wet pulp that have been dried to a moisture content lower than about 65-75%.

As a further alternative, the solid fraction obtained from the carbonation process could be combined with the pulp and this mixture constitutes the processed sugar beet root product from which the plant extract is obtained.

A preferred aspect of the embodiments relates to a plant extract comprising at least one phenolic compound. The plant extract is obtainable from a solid fraction of carbonated sugar beet root juice. Hence, in this preferred aspect the plant extract is obtainable from a processed sugar beet root product in the form of the solid fraction of carbonated sugar beet root juice.

In an embodiment, the plant extract is obtained from the solid fraction of carbonated sugar beet root juice.

The solid fraction of the carbonated sugar beet root juice is preferably, as indicated above, obtained from a process comprising slicing sugar beet root and producing sugar beet root juice from the sliced sugar beet root. The sugar beet root juice is then carbonated to form the solid fraction of the carbonated sugar beet root juice.

In a particular embodiment, carbonating the sugar beet root juice preferably comprises, as indicated above, mixing the sugar beet root juice with a suspension of calcium hydroxide in water to form an alkaline sugar solution. Carbon dioxide is bubbled through the alkaline sugar solution to precipitate the calcium hydroxide as calcium carbonate particles entrapping and absorbing impurities in the sugar beet root juice. The liquid fraction is then removed to form the solid fraction of carbonated sugar beet root juice.

In an embodiment, the plant extract of the embodiments is obtainable according to a process comprising mixing a solvent with the sugar beet root and/or the processed sugar beet root product, preferably the solid fraction of carbonated sugar beet root juice. The mixture is allowed to settle in a tank or other reservoir or container to form a supernatant and settled solids, preferably, in the form of the solid fraction of carbonated sugar beet root juice. The supernatant is separated from the settled solids, such as by decanting the supernatant from the solids or sucking off, i.e. aspirating, the supernatant, leaving the solids at the bottom of the tank. The phenolic-containing plant extract of the embodiments is produced from this supernatant.

In an embodiment, extraction is preferably allowed to continue for at least 30 minutes, i.e. the supernatant is removed from the mixture between the solid fraction of carbonated sugar beet root juice and the solvent preferably following at least 30 minutes of extraction. Experimental data indicates that the phenolic content of the sugar beet extract is substantially the same following 2 hours of extraction as compared to 24 hours of extraction. However, salts are generally extracted at a slower rate and the sugar beet extract obtained with 24 hours of extraction generally has a higher salt concentration as compared to the sugar beet extract obtained with 2 hours of extraction, see Table 1. In a preferred embodiment, extraction is thereby taking place for a time period within an interval of at least 30 minutes up to 24 hours, preferably from 1 hour up to 6 hours, such as from 1 hour up to 4 hours or from 1 hour up to 3 hours. A typical example is to use an extraction time of 1-2 hours, such as about 2 hours.

In an embodiment, the supernatant could be used directly as plant extract according to the embodiments.

In another embodiment, the supernatant is diluted, such as by adding, the same solvent that was used during the extraction step, i.e. mixed with the (processed) sugar beet root (product), or another solvent to form the plant extract.

In a further embodiment, the supernatant is concentrated, for instance by evaporation of a portion of the solvent, to form the plant extract.

In a particular embodiment the supernatant is filtered once or multiple times, such as twice, to remove any suspended particles from the supernatant. The filtered supernatant could then be used as plant extract. In an optional but preferred step the filtered supernatant is centrifuged to form a pellet of suspended particles that were not removed during the filtering step(s). The supernatant is separated from this pellet and used as plant extract in liquid form. Optional dilution or concentration can be done as mentioned above.

The solvent used in the method of producing the plant extract is preferably selected from a group consisting of water, ethanol, methanol and combinations thereof. In a particular embodiment, the solvent is ethanol or a combination of water and ethanol, such as 99.9% ethanol.

If the plant extract is to be diluted, as mentioned above, the solvent could be selected from the group mentioned above, i.e. water, ethanol, methanol or any combination thereof.

The plant extract of the embodiments comprises at least one phenolic compound extracted from the sugar beet. In a particular embodiment, the plant extract comprises a mixture of different phenolic compounds. The plant extract preferably comprises p-hydroxybenzoic acid, vanillic acid and epicatechin gallate. The plant extract more preferably comprises these three compounds as the main phenolic compounds.

p-Hydroxybenzoic acid, also referred to as 4-hydroxybenzoic acid, is a phenolic derivative of benzoic acid. p-Hydroxybenzoic acid is a popular antioxidant. Vanillic acid, also referred to as 4-hydroxy-3-methoxybenzoic acid, is a dihydroxybenzoic acid derivative traditionally used as a flavoring agent. Epicatechin gallate is a flavan-3-ol (flavonoid) traditionally found in green tea, buckwheat and in grape.

In an embodiment, the plant extract comprises, in addition to, p-hydroxybenzoic acid, vanillic acid and epicatechin gallate at least one of isoferulic acid and cinnamic acid, preferably both isoferulic acid and cinnamic acid.

In an embodiment, the plant extract comprises p-hydroxybenzoic acid at a concentration of more than 5 µg/ml. In more preferred embodiment, the plant extract comprises p-hydroxybenzoic acid at a concentration of at least 10 µg/ml. The concentrations of p-hydroxybenzoic acid as stated above are preferably the concentration of the phenolic compound in the plant extract as working solution, i.e. as adapted to or intended to be applied to a plant.

Experimental data as presented herein indicates at a concentration of p-hydroxybenzoic acid of 5 µg/ml or lower will not induce any positive effects to plants, whereas a concentration above 5 µg/ml and in particular equal to or higher than 10 µg/ml is capable of inducing protection of a plant against plant pathogens.

Another aspect of the embodiments, therefore, relates to a plant extract comprising p-hydroxybenzoic acid at a concentration of more than 5 µg/ml and preferably at least 10 µg/ml. The plant extract is obtainable from a sugar beet root and/or a processed sugar beet root product, preferably a processed sugar beet root product, and more preferably a solid fraction of carbonated sugar beet root juice.

The plant extract of the embodiments preferably comprises various ions in addition to the phenolic compounds. In a particular embodiment, the main ions are potassium ($K^+$) and calcium ($Ca^{2+}$) ions.

In a particular embodiment, the plant extract comprises natural elements at the following concentrations, see Table 1:

Al at a concentration of 0.02-0.03 mg/l;
B at a concentration of 0.3-0.4 mg/l;
Ca at a concentration of 6-18 mg/ml;
Cu at a concentration of 0.05-0.11 mg/l;
Fe at a concentration of 0.10-0.18 mg/l;
K at a concentration of 34-68 mg/l;
Mg at a concentration of 0.33-1.1 mg/l;
Mn at a concentration of 0.03-0.06 mg/l;
Mo at a concentration of 0.0008-0.0017 mg/l;
Na at a concentration of 3.4-6.5 mg/ml;
S at a concentration of 4.4-4.8 mg/l;
Se at a concentration of 0.8-1 mg/l; and
Zn at a concentration of 0.05-0.15 mg/l of the plant extract in undiluted form.

In a preferred embodiment, the plant extract is obtained from a 2 hours extraction corresponding to SBE (100%), 2 h extr in Table 1.

The plant extract of the embodiments is adapted to protect a plant against an infection of a plant pathogen. However, the plant extract is preferably not toxic to the plant pathogen at a working concentration adapted to be applied to the plant.

Another aspect of the embodiments relates to a plant extract comprising at least one phenolic compound and obtainable from a sugar beet root and/or a processed sugar beet root product, preferably a processed sugar beet root product, and more preferably a solid fraction of carbonated sugar beet root juice. In this aspect, the plant extract is adapted to protect a plant against an infection of a plant pathogen. However, the plant extract is not toxic to the plant pathogen at a working solution adapted to be applied to the plant.

The plant extract of the embodiments can be used, optionally in diluted or concentrated form, directly in the various methods to be further disclosed herein. Alternatively, the plant extract is used to form a composition comprising, in addition, to the plant extract at least one plant signaling agent and/or at least one fungicide and/or bactericide. The plant signaling agent and/or fungicide and/or bactericide can be selected from agents and/or fungicides and/or bactericides traditionally used to induce resistance to biotic stresses in a plant and/or treat or inhibit plant diseases, such as late blight disease. Non-limiting examples of such agents include the fungicides Shirlan®, Ranman® and Aliette® and benzothiadiazole (BTH), which is an inducer of systemic acquired resistance and disease resistance in plants.

The composition may additionally comprise a vehicle, preferably a liquid vehicle. The vehicle could be the solvent used when producing the plant extract. The composition is preferably formulated as a foliar spray. Such a composition formulation can easily be applied to plants. Other formulations are possible and encompassed by the embodiments.

In an aspect the plant extract or the composition is used in a method of inducing resistance to a biotic stress in a plant. The method comprises applying the plant extract and/or composition to the plant. The applying step could be performed according to various embodiments. For instance, the plant extract or composition could be sprayed on the plant, watered on the plant, added to the substrate, such as soil, peat, compost, vermiculite, perlite, sand or clay, in which the plant is growing, etc.

The biotic stress is preferably caused by a *Phytophthora oomycte*. *Phytophthora* is a genus of plant-damaging water molds, whose member species are capable of causing enormous economic losses on crops worldwide. Examples of *Phytophtora* diseases include:

*Phytophthora cactorum* causing rhododendron root rot affecting rhododendrons, azaleas and causing bleeding canker in hardwood trees;

*Phytophthora cambivora* causing Ink disease in European Chestnut trees;

*Phytophthora capsici* infecting Cucurbitaceae fruits, such as cucumbers and squash;

*Phytophthora cinnamoni* causing cinnamon root rot affecting arborvitae, azalea, Chamaecyparis, dogwood, forsythia, Fraser fir, hemlock, Japanese holly, juniper, Pieris, rhododendron, Taxus, white pine, American chestnut and Australian Jaffa;

*Phytophthora fragariae* causing red root rot affecting strawberries;

*Phytophthora kernoviae*, which is a pathogen of beech and rhododendron, also occurring on other trees and shrubs including oak, and holm oak;

*Phytophthora megakarya*, which is one of the cocoa black pod disease species;

*Phytophthora palmivora* causing fruit rot in coconuts and betel nuts;

*Phytophthora plurivora* affecting Beech trees;

*Phytophthora ramorum* infecting over 60 plant genera and over 100 host species;

*Phytophthora quercina* causing oak death;

*Phytophthora sojae* causing soybean root rot; and

*Phytophthora infestans* causing late blight disease on potato and tomato, also referred to as potato blight as well as brown rot on potato tubers.

In a preferred embodiment, the biotic stress is caused by *Phytophtora infestans*.

Another aspect of the embodiments relates to a method of treating or preventing, or at least inhibiting or alleviating, late blight disease in a plant. The method comprises applying the plant extract and/or composition to the plant. The applying step can be performed as discussed above, such as by spraying or watering.

The late blight disease is preferably due to an infection by *Phytophtora infestans*.

The plant that can be treated according to the aspects of the embodiments can be any plant, including monocots (monocotyledon) and dicots (dicotyledons) as well as trees. In a preferred embodiment, the plant belongs to the Solanaceae family. The plant is more preferably *Solanum tuberosum*, i.e. potato.

The plant extract of the embodiments differs from the prior art techniques mentioned in the background section since it uses an extract from sugar beet root. The sugar beet extract (SBE) comprises a mixture of phenolic compounds and natural elements that reduce the size of *Phytophthora infestans* infection lesions in potato without being toxic to the plant or the pathogen. Because the SBE is a clear liquid, it is possible to combine it with fungicides and/or bactericides. An additional advantage is that the SBE may be based on a raw product already cycled to the agricultural system. Maybe the most important difference from existing formulations is that the SBE may be based on a waste plant material that is available at large volumes with consistent quality.

A further aspect of the embodiment relates to a method of producing a plant extract comprising at least one phenolic compound. The method comprises mixing a solvent with a sugar beet root and/or a processed sugar beet root product, preferably a solid fraction of carbonated sugar beet root juice. The mixture is allowed to settle to form supernatant and settled solids, which in a preferred embodiment corresponds to the solid fraction of carbonated sugar beet root juice. The supernatant is separated from the solids and used to produce the plant extract.

The method optionally comprises the previously discussed filtering step(s) and/or centrifuging step. The processed sugar beet root product can be obtained as previously disclosed herein. Thus, the optionally washed sugar beet root is sliced to form the sliced sugar beet root, i.e. so called cossettes. Sugar beet root juice (raw juice) is produced from the sliced sugar beet root, such as in a diffuser, leaving the remaining semi-solid sugar beet root material. If the processed sugar beet root material is the solid fraction of carbonated sugar beet root juice the method comprises carbonating the raw juice to form the carbonated sugar beet root juice as solid material from which the plant extract can be produced. The carbonation is preferably performed using hot lime milk and carbon dioxide as previously disclosed herein.

However, if the processed sugar beet root product is in the form of pulp the method instead comprises pressing the sliced beet root material after removing the raw juice to form the sugar beet root pulp. This pulp may optionally be dried before extracting the plant extract therefrom.

The mixture between the solvent and the solid fraction of carbonated sugar beet root juice is preferably allowed to stand for a selected extraction time period, as previously defined herein, before the supernatant is separated from the solids.

The examples shown here below have the sole aim of exemplifying one of the numerous results of the embodiment, however, without limiting it, as similar results are within the scope of the embodiments.

EXAMPLES

Extraction Process

During the sugar refining process, sugar beets are washed and then sliced. After this, a raw juice was prepared, which underwent purification when mixed with lime in order to precipitate nutrients and organic materials. The juice-lime slurry was carbonated and thereby aggregates were formed that sediment. This solid fraction was pressed to a humidity of 65%. The pressed solid fraction is typically sold back to the farmer as soil amendment mainly for increasing the pH and as a nitrogen source. This solid material is normally spread on the soil in late autumn or in the winter. We used this solid fraction in our study as the starting material for the extraction. It was collected in bags and was stored in a cold room (8° C.) until use. A sugar beet extract (SBE) was obtained by mixing 0.5 l of 99.9% ethanol to 1 000 g of the solid material. The mixture was thoroughly blended and left for 2 hours, to settle in a cold room. After settling, a layer of yellowish supernatant was formed and carefully separated from the slurry and filtered with two layers of cheesecloth to get rid of the suspended particles present in the liquid. The filtrate was then subjected to centrifugation (3 000 rpm, 3 minutes at 5° C.). After centrifugation, the supernatant was stored in screw-capped containers at 8° C. until use. Before plant treatment, the extract was diluted five-fold with distilled water.

Extract Composition

In order to investigate some compounds present in the SBE, it was subjected to HPLC analysis using a Merck Hitachi LaChrom HPLC system consisting of a D-7100 pump, D-7200 autosampler, D-7300 column oven (set at 40° C.) and a D-7455 DAD detector scanning the absorbance between 220 and 400 nm. Five hundred µl of the extract was evaporated to dryness and dissolved in 100 µl of methanol and 50 µl water. Separation on an Aquasil C18 column (Thermo Scientific, Waltham, Mass., USA) was achieved using a gradient of water (acidified with o-phosphoric acid to pH 3; A) and methanol (B) as follows: 0% B (0-1 minute); 5-45% B (1-15 minutes); 45-85% B (15-20 minutes); 85% B (20-23 minutes) and 85-100% B (23-25 minutes), 100% B (25-27 minutes), followed by equilibration to initial conditions. The flow rate was 0.8 ml/min and the injection volume was 40 µl. The peak area data were collected at 280 nm, allowing quantification of simple phenolics, phenolic acids and flavonoids. UV-spectrum collected at 200 to 400 nm were compared to spectral data in a standard compound library and the compounds were tentatively identified if their spectrum exhibited a match of 97% or better against that of an authentic standard.

Figure 5:
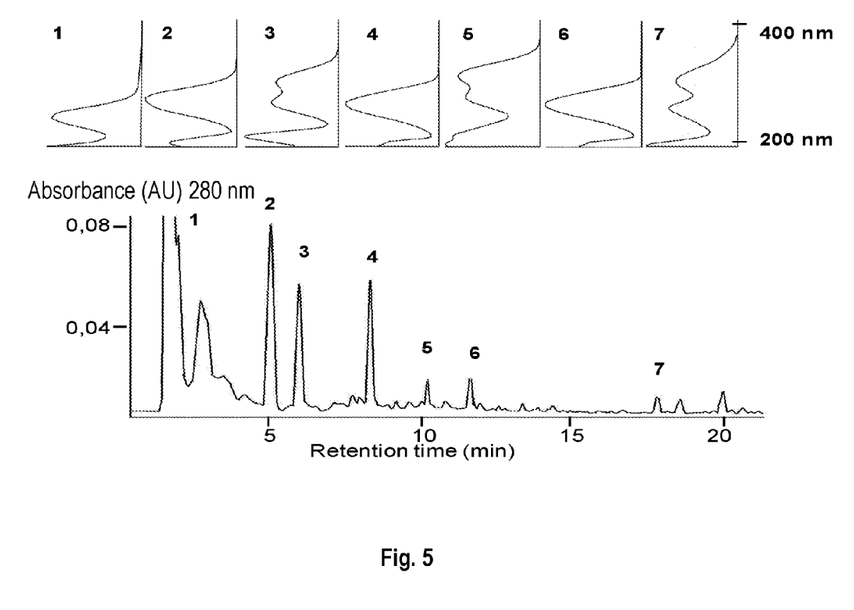
Figure 6:
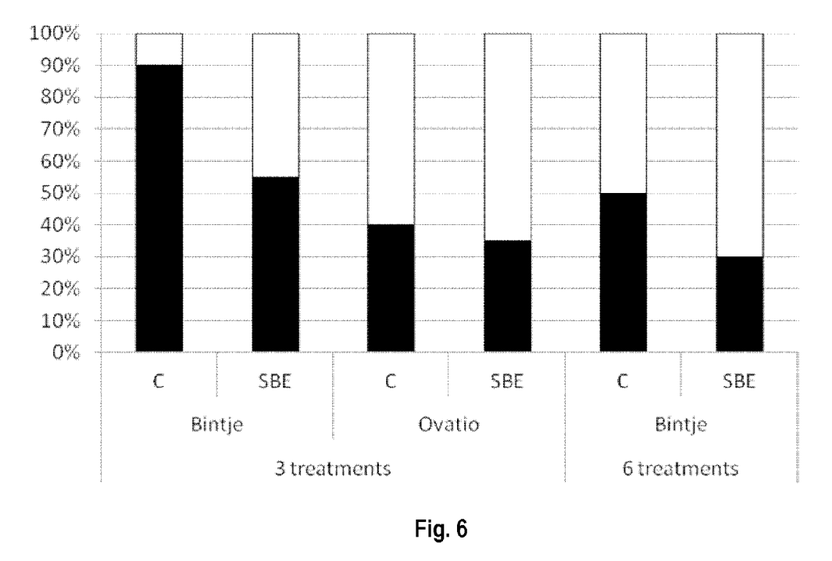
Figure 7A:
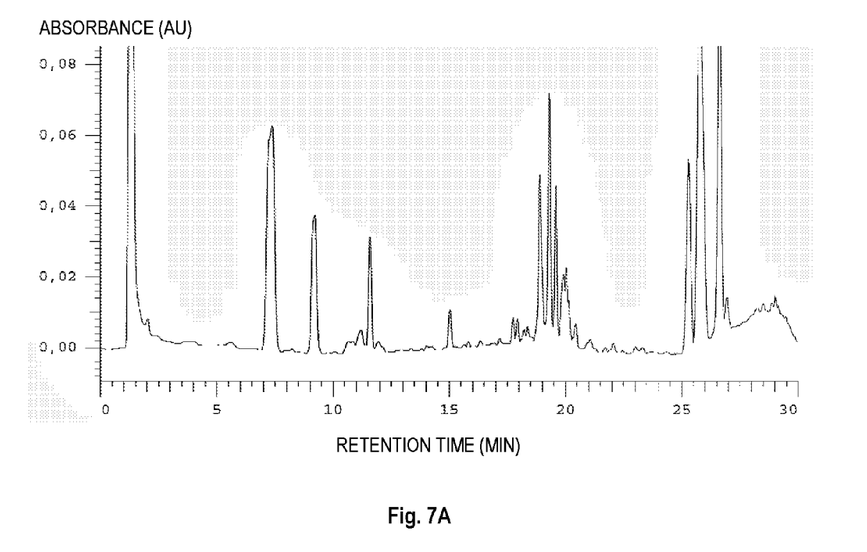
Figure 7B:
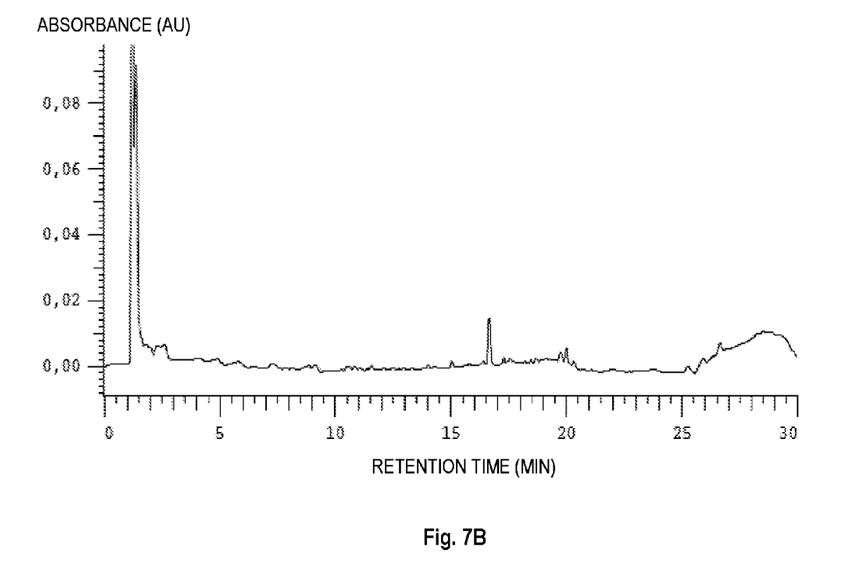

Several compounds absorbing at the UV-range were detected in the extract. The HPLC analysis of the SBE identified a number of phenolic compounds (FIG. 5). Peaks separated under analysis conditions were identified as p-hydroxybenzoic acid (peak 1), vanillic acid (peak 2), epicatechin gallate (peak 3), isoferulic acid (peak 4) and cinnamic acid (peak 6).

Natural element concentrations in the extract were analyzed by the standard methods at Lund University according to (Tyler and Olsson 2006). Many natural elements were detected in the extract as shown by the concentrations in mg/l listed in Table 1. These natural elements may contribute to the protective effect of the SBE.

TABLE 1

Natural element analysis in mg/l of SBE by the standard methods

| | Al | B | Ca | Cd | Cu | Fe | K |
|---|---|---|---|---|---|---|---|
| SBE(100%), 2 h extr | 0.03 | 0.28 | 6.08 | 0.00035 | 0.05 | 0.10 | 34.30 |
| SBE over night extr | 0.02 | 0.48 | 17.86 | 0.00244 | 0.11 | 0.18 | 68.20 |

| | Mg | Mn | Mo | Na | Ni | S | Sb |
|---|---|---|---|---|---|---|---|
| SBE(100%), 2 h extr | 0.33 | 0.03 | 0.0017 | 3.38 | 0.01 | 4.77 | 0.11 |
| SBE over night extr | 1.12 | 0.06 | 0.0008 | 6.48 | 0.02 | 4.45 | 0.07 |

| | Se | Zn | Cl | $NO_3$—N | $SO_4$—S |
|---|---|---|---|---|---|
| SBE(100%), 2 h extr | 1.06 | 0.05 | 2.40 | 0.58 | 0.05 |
| SBE over night extr | 0.80 | 0.15 | 5.16 | 0.85 | 0.59 |

Treatment of Plants Against Infection

Plant Cultivation—

Three potato (*Solanum tuberosum*) cultivars were used in this study: Desiree and Bintje that are susceptible to *P. infestans* and Ovatio which shows partial resistance. The tubers were planted in 5 l plastic pots with peat-based soil (Weibull Horto, Sweden) that are supplemented with 3 kg/m³ dolomite lime, 3 kg/m³ limestone, 0.7 kg/m³ PG-mix™ fertilizer (NPKA+micronutrients) and 120 kg/m³ sand (1-3 mm). The pots were placed in a greenhouse chamber with controlled conditions. The temperature was 20° C. during day and 15° C. during night with 16 hours of exposure to natural light supplemented with high-pressure sodium lamps. The plants were used after four weeks of cultivation. For PR-1 protein analysis, plants were grown for four weeks in a chamber with only 16 h artificial light (300 μmol/m²s) at 20° C.

*Phytophthora infestans* Growth—

The *P. infestans* isolate SE030558 (mating type A1, virulent on plants carrying R1, R3, R4, R7, R10, R11, R denotes a resistance gene) used is highly virulent. Cultures were maintained on pea agar medium according to standard protocols. In order to obtain infectious sporangia, *P. infestans* was grown and maintained on detached leaves of the potato cultivar Desiree or Bintje in sealed plastic boxes containing moist filter papers. The boxes were kept at 15° C. with the following light regime: 16 h light and 8 h dark. Sporangia were released by vigorously shaking one infected leaf in 10-15 ml distilled water. The concentration of the sporangia was set to 15 000 sporangia/ml using a Fuchs-Rosenthal counting chamber. The sporangial solution was kept at 4° C. for 2 hours before the inoculation experiment in order to induce zoospore release.

Inoculation:

Fully expanded leaves of 4-week-old plants were put in boxes, and inoculated with *P. infestans* by adding 20 μl of the sporangial suspension and the boxes were kept as mentioned earlier. Measurements of lesion diameter were done six days post infection (dpi).

Direct Toxicity Bioassays—

Hyphal growth bioassay was done by an agar disc diffusion bioassay (Röhner et al. 2004). *P. infestans* was grown on pea agar plates after transfer of mycelia plugs which had been growing on pea agar plates for 3 weeks. Seven days after initiation of the hyphal growth, sterile paper discs (12 mm diameter) were placed 5 mm outside the opposite edge of a hyphal colony of *P. infestans* growing on pea agar medium. An aliquot of 80 μl of 20% SBE or distilled water were put on the paper disc and the plates were sealed with parafilm after evaporation of the liquid. After 2 and 3 days of incubation in the dark at 18° C., the hyphal growth surrounding the sites of impregnated paper discs was evaluated. In order to measure sporangia germination inhibition Petri dishes containing *P. infestans* grown for 17-20 days on pea agar medium were flooded with sterile deionized water and the hyphal growth was gently scraped with a plastic scraper in order to release the sporangia. The solution was first filtered with two layers of cheese cloth to get rid of the hyphal material and the density of sporangia was checked with a Fuchs-Rosenthal chamber and the solution was later filtered again through a 100 μm cell strainer. A more concentrated suspension of sporangia was made by centrifugation of the sporangial solution at 3 000 rpm for 3 minutes. In order to test the effect of SBE (final concentration 20%) on the direct germination of sporangia, SBE solution was first concentrated. 1 ml of undiluted SBE were run in a rotary evaporator at room temperature in order to concentrate the SBE to 50 μl and a stock solution of 30% SBE with low ethanol concentration was made by adding sterile distilled water. To test the effect of the SBE on direct germination of sporangia, 1 ml in Eppendorf tubes (three replicates for each treatment) was made so that the final concentration of SBE was 20% (same as with the leaf treatments) and sporangia was 40 000 sporangia/ml. The final concentration of ethanol was maximum 1% and therefore 1% ethanol (EtOH) was used as a control treatment. The samples were put in a box and wrapped with wet paper. Then the box was wrapped in aluminum foil and put in an incubator at 21° C. for one day. The percentage of sporangia germination was calculated by counting germinated and non-germinated sporangia in four randomly chosen microscopic fields. The average percentage of germination was calculated from three replicates of each treatment.

Sporangia Production in the Infected Leaves—

The day after the last spraying of plants with water, SBE, or BABA, fully expanded leaves were detached and inoculated with *P. infestans* (15 000 sporangia/ml) in the detached leaf assay as described earlier. Ten days after infection, each of the infected leaves (12 in total) was placed in a 50 ml Falcon tube containing 15 ml distilled water, and the samples were shaken (3 000 rpm for 10 minutes) to release sporangia. The number of sporangia was counted using a Fuchs-Rosenthal chamber. The experiment was repeated twice.

Extraction of Apoplastic Fluid—

Leaf sampling was done by taking fully expanded leaves from four-week old plants. The leaves were dipped in 1% Tween-20 solution for 10 seconds and then were dried quickly on paper. The leaves with their abaxial side up were then placed in Petri dishes and immersed with phosphate buffer saline (150 mM sodium phosphate and 50 mM sodium chloride). Metal nets were put on the leaves to better submerge the leaves in the buffer and were placed in a vacuum chamber for 10 minutes. Afterwards, the leaves were briefly blotted on paper, rolled and inserted carefully into 15 ml Falcon tubes on ice to which 3.5 μl of a protease inhibitor cocktail (Sigma-Aldrich) and a hollow metal ring were added at the bottom of each tube. Adding the metal ring separated the leaves from the apoplastic fluid accumulating at the bottom of the tube. The samples were centrifuged at 3 000 rpm for 3 minutes at 4° C. and the apoplastic fluid were stored at −80° C. The experiment was repeated twice with similar results.

SDS-PAGE Separation—

In order to separate the apoplastic proteins, 12% SDS-PAGE was used. The proteins were denaturated with 6× sample buffer (0.5 M Tris, 30% glycerol, 10% SDS and 0.012% bromophenol blue) and dithiothreitol at a final concentration of 0.1 M by heating at 65° C. for 10 minutes.

Treatment of Plants with Extract—

Just before the experiments started, the SBE was diluted five-fold with distilled water. Each potato genotype was exposed to four different treatments. Three replicate plants from each of the three genotypes (in total twelve plants from each different genotype were sprayed with four different agents) were exposed to one of the following spraying agents: SBE (diluted to 20%), BABA (Sigma-Aldrich, 0.3 g/l), 20% ethanol (EtOH), or distilled water. For each potato plant, 100-200 ml of the spraying agent was sprayed with a hand pressure sprayer until the agent ran off. Spraying was done two times intervened by one day. Leaf sampling was done one day after the last spraying treatment. Potatoes were planted in the field in two sets. Half were untreated control plant and the second half were sprayed with 20% SBE three times with one week interval. 20 leaves from each variety and treatment were randomly picked for *Phytophthora* infection in lab. Bintje plants were sprayed with 20% SBE for another three times with one week interval.

Application of SBE Decreased the Size of the Infection Lesions

Figure 1A:
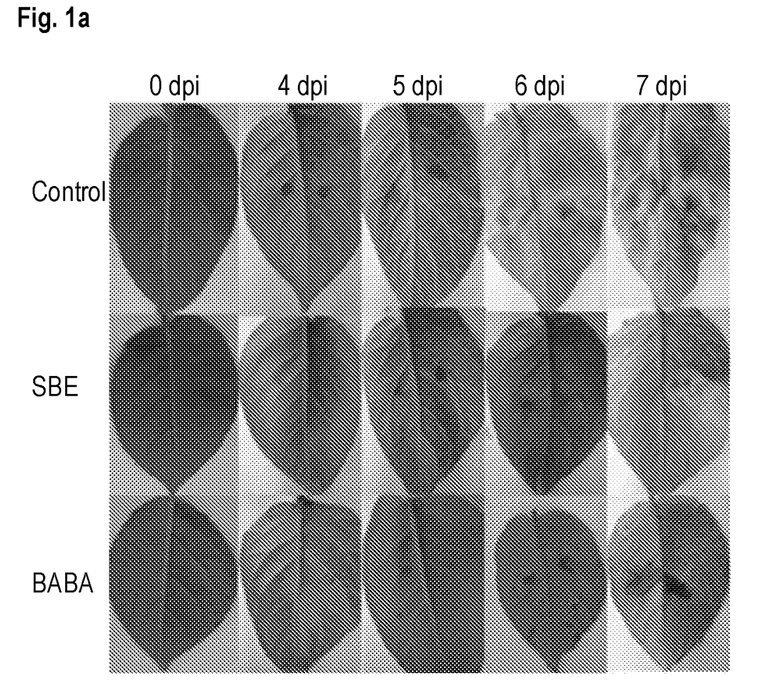
FIG. 1a illustrates lesion size appearance 4-7 days post infection (dpi) for Desiree plants sprayed with tap water (control), sugar beet extract (SBE) (20% in tap water), and BABA (β-aminobutyric acid, 0.3 g/l in tap water), inoculated with *P. infestans* (15 000 sporangia/ml) in a detached leaf assay from greenhouse-grown plants. The small necrotic dots on the BABA-treated leaves were only detected in that treatment.
Figure 1B:
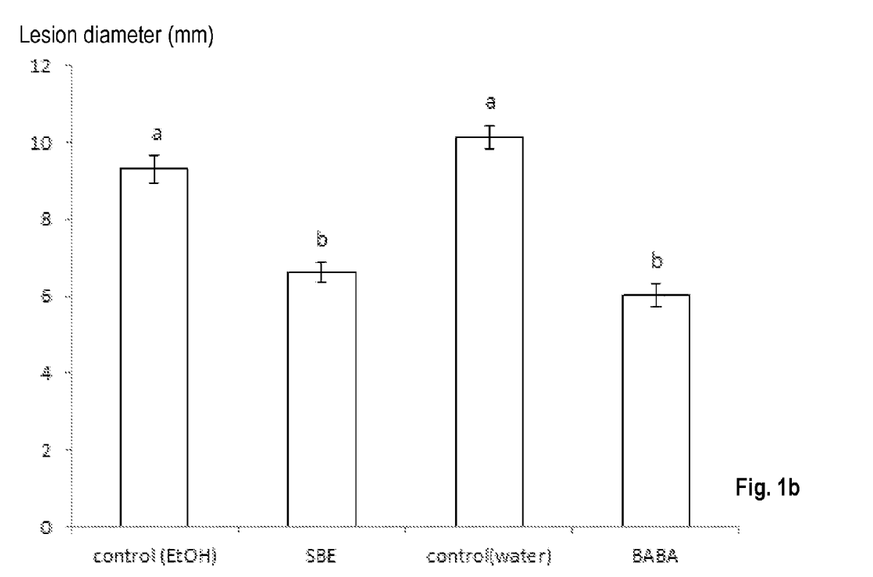
Figure 1C:
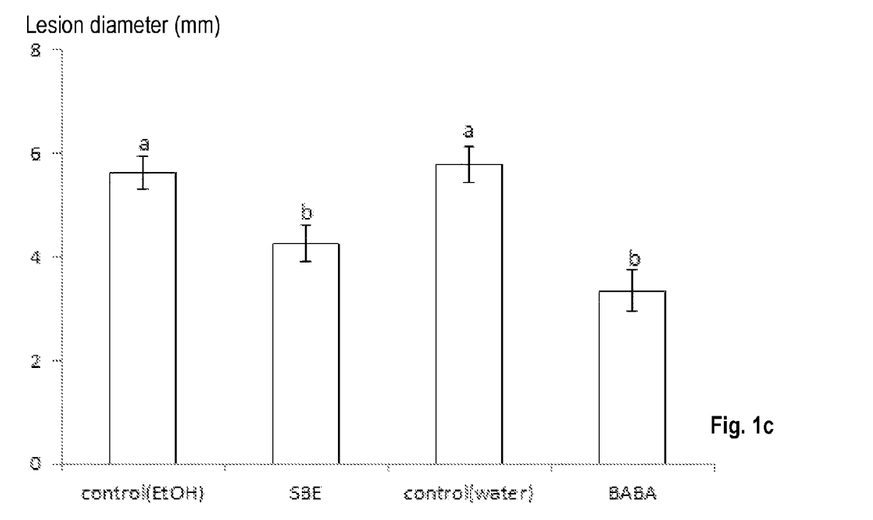
Figure 1D:
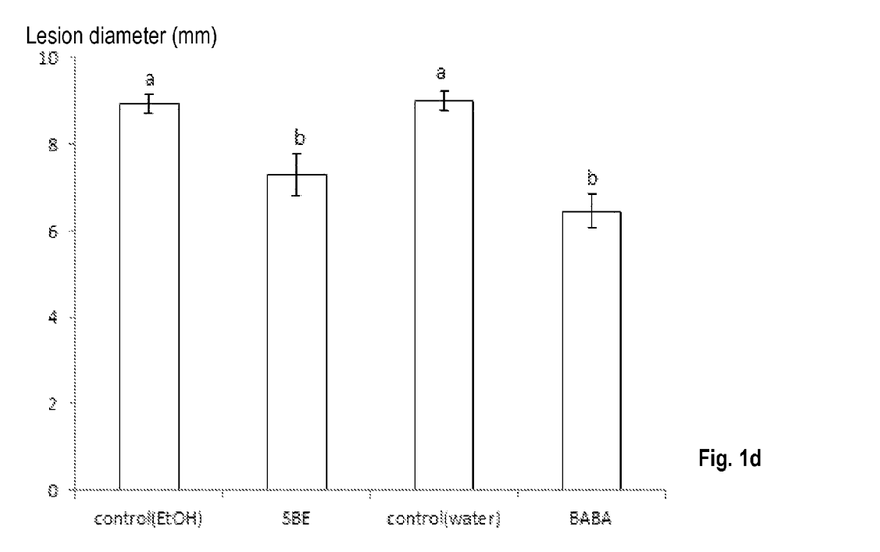

SBE application decreased the macroscopic growth of the infection lesions as demonstrated by assays on detached leaves of Desiree plants as compared to the control leaves sprayed with water only (FIG. 1*a*). After quantification, significant reductions of infection lesion (15-18%) were found in all three potato genotypes after the SBE application (FIGS. 1*b*, 1*c* and 1*d*). The controls with 20% ethanol or water did not differ, and the effect of SBE was not significantly different from the result from BABA-treated plants (FIGS. 1*b*, 1*c* and 1*d*). Small necrotic dots or lesions, characteristic of BABA treatments, were visible two days after BABA treatment on Desiree plants and to a lesser extent on Ovatio, while no such lesions were observed on Bintje plants. SBE-treated leaves did not exhibit necrotic lesions.

SBE Decreased Sporangia Production

Figure 2:
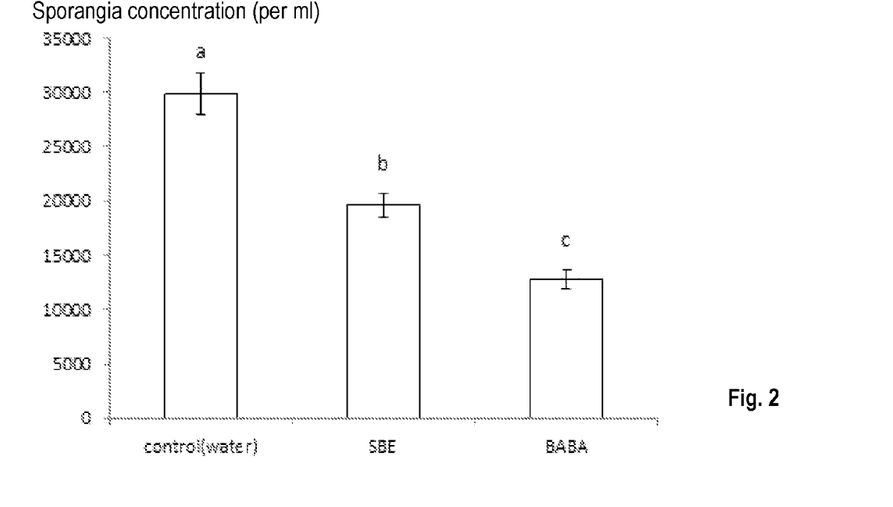

The reduced growth of the infection lesions which was seen after the SBE treatment could be caused by the reduced sporangia production in the infected treated leaves. Sporangia are the infectious propagules that start the disease cycle in nature. Thus, the rate of sporangia production can have important implications because it contributes to the overall epidemiology of the late blight disease. Sporangia production was estimated in the infected leaves taken from different treatments. A reduced sporangia production was noticed in the leaves taken from the SBE-treated Desiree plants compared to the control leaves from the water-treated plants (FIG. 2).

SBE had No Direct Toxic Effect on *P. infestans*

Figure 3A:
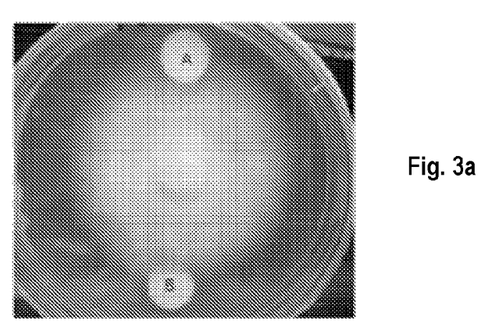
Figure 3B:
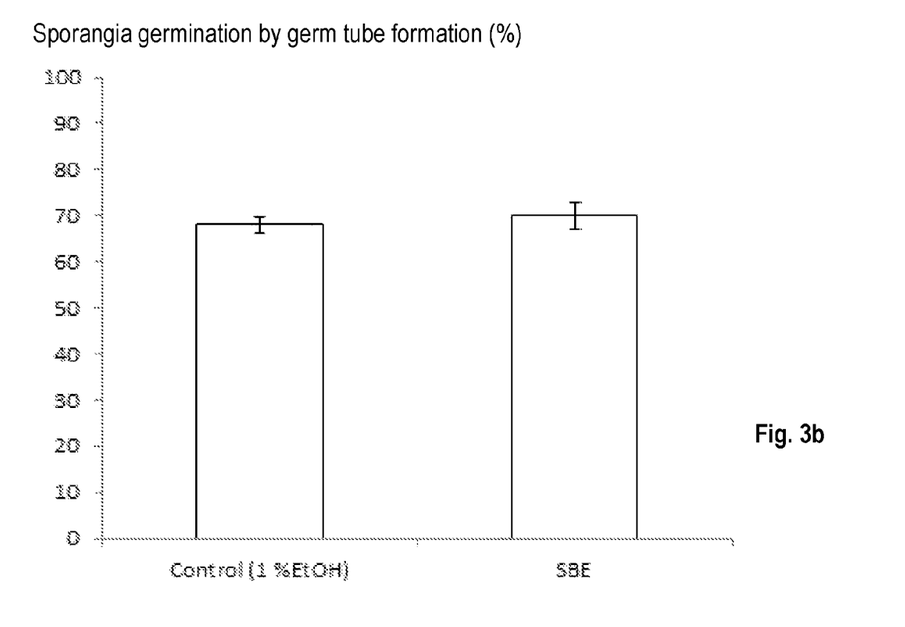
Figure 4:
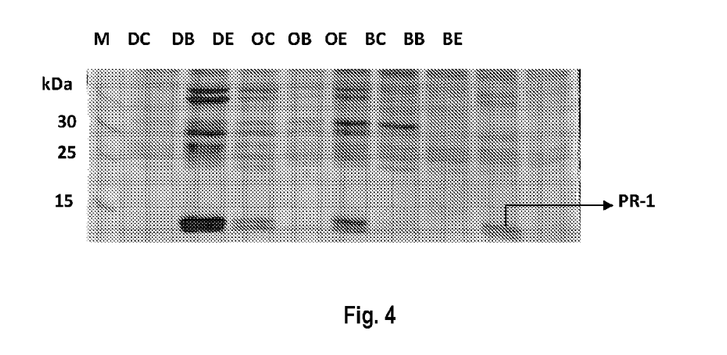

It is possible that the effect of reduced lesion development and sporangia production that was observed after SBE treatment might have resulted from a direct toxic effect of the extract on the germination of sporangia or hyphal growth. However, after the SBE addition, no direct toxic effect of the SBE on the hyphal growth of *P. infestans* was found (FIG. 3*a*). Moreover, sporangia germinated normally in the presence of the SBE as revealed by the microscopic examination of the germinated sporangia (FIG. 3*b*).

PR-1 Protein Induction after SBE Treatment

Since no direct effect on the pathogen was detected by SBE treatment, we tested if induced resistance pathways in the host were activated after SBE treatment. Pathogenesis-related protein (PR-1) accumulation in the apoplast was used as a marker for this. One day after the last spraying treatment with SBE, PR-1 protein induction was found to be strongest in the leaves of Desiree, less strong in Ovatio and weakest in Bintje (FIG. 4). A similar pattern was also evident after BABA treatment although the induction overall was stronger after BABA application. Other secreted proteins were also found to accumulate after SBE and BABA treatment. Thus, SBE was able to induce protein-based defense pathways.

Application of SBE in Field Trial Decreased *Phytophthora* Infection

Bintje and Ovatio were planted in the field at the SLU Alnarp campus, Sweden, in two sets. 50 tubers from each variety were used. Fifty percent of the plants were left as untreated control plants and the second half were sprayed with 20% SBE (sugar beet extract) three times with one week interval. 20 leaves from each variety and treatment were randomly picked for *Phytophthora* infection (FIG. 6). Pretreatment of plants with SBE resulted in a reduced percent of infected leaves 11 days after infection. Surprisingly, the largest effect was in Bintje, and not in the partially resistant cultivar (Ovatio). In Bintje sprayed with SBE for an additional three times with one week interval (6 treatments in total), the fraction of successfully infected leaves were reduced in a similar level as after 3 treatments (FIG. 6).

Defense inducing agents could cause reduction in yield as these agents can affect the stress physiology of the plants. However, no reduction in potato tuber yield could be detected between control plants and plants sprayed with SBE (25 control Bintje (505 tubers, 29 Kg) and, 25 sprayed (507 tubers, 32 kg)).

Comparative Study of SBE, Elot-Vis® and Sugar Beet Fiber Extract

A field of grown cv Bintje at SLU Alnarp campus, Sweden was divided into five separate blocks and in each block treatments were independently randomized into five rows. In total 25 rows were used separated by 70 cm. In each row 8 plants, separated by 30 cm, were grown. Treatments were 20% ethanol (control), SBE, half dose of SBE (0.5× SBE), extract from Speedi-Beet and Elot-Vis® (dose as recommended by manufacturer) using 400 ml of treatment solution per row. The day following the $5^{th}$ treatment, samples were taken for detached leaf assay.

The extract from Speedi-Beet was a 20% ethanol extract from the product Speedi Beet manufactured by Masham Micronized Feeds, UK. Basically, Speedi-Beet is unmolassed sugar beet pulp cooked via a unique process to produce flakes. The product has high fiber content but is low in sugar and starch. Speedi-Beet is used as horse feed. The extract was made using the same extraction method as previously disclosed herein for SEB.

Table 2 below illustrates lesion size of *Phytophtora infestans* measured seven days after infection. Two tailed Student-T test were used for statistical analysis (n=12, p<0.05 regarded as statistically significant).

TABLE 2 comparative study of field-grown cv Bintje

| Treatment | Symptoms of infection | Significant different from control | Tested not significant different from each other |
|---|---|---|---|
| SBE | 80% | a (p = 0.0015) | b |
| Elot-vis ® | 73% | a (p = 0.0003) | b |
| Control | 100% | | — |
| 0.5 × SBE | 86% | | — |
| Speedi-Beet extract | 90% | | — |

Thus, the SBE product of the embodiments obtained from the solid fraction of carbonated sugar beet root juice had a significant effect in terms of reducing the symptoms of *Phytophtora infestans* infection in Bintje as compared to control. It is further shown in this field experiment that a plant extract obtained from another fraction of sugar beet raw material, i.e. the Speedi-beet extract, was not significantly different from control.

Hence, the present field study shows that different plant extract fractions obtain from sugar beet have different effects in inducing resistance to *Phytophtora infestans* infection in Bintje and therefore have different constituents. This is further shown in FIGS. 7A and 7B, where High-Performance Liquid Chromatography (HPLC) chromatograms (absorbance 280 nm) of SBE, see FIG. 7A, and the Speedi-Beet extract, see FIG. 7B. HPLC analysis was conducted as previously disclosed herein.

The figures clearly indicates that the two different sugar beet extracts, SBE and Speedi-Beet extract, have significantly different constitutents and in particular different phenolic content. The total phenolic content of SBE was estimated from the chromatogram to be about 674 µg/ml, whereas the Speedi-Beet extract had an estimated total phenolic content of merely 88 µg/ml.

The field study further showed that there was no significant difference in technical effect between SBE of the embodiments and the commercially available Elot-Vis®. However, a clear difference between SBE and Elot-Vis® is that Elot-Vis® is toxic to *Phytophtora infestans*, whereas SBE is not. Hence, whereas Elot-Vis® achieve symptom reduction by being toxic to *Phytophtora infestans*, SBE instead has a different mode of action by immunoboosting the natural defense in Bintje against *Phytophtora infestans.*

The total concentration of p-hydroxybenzoic acid (pOHBA) in the SBE content was determined by integration of area of pOHBA peaks in the HPLC chromatogram and comparison with pOHBA standards. The results indicated a concentration of pOHBA of 10 μg/ml in the 20% SBE. As shown in Table 2, a sugar beet extract of the embodiments (SBE) with a pOHBA content of at least 10 ρg/ml showed significant effect on *Phytophtora infestans* infection in Bintje. Furthermore, dilution of the 20% ethanol SBE to half concentration (0.5×SBE) resulted in no significant difference as compared to control. Hence, it seems that a pOHBA concentration of 5 μg/ml in the sugar beet extract (0.5×SBE) might be too low to achieve significant effect on *Phytophtora infestans* infection in Bintje.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

Coquoz et al. (1995), *Phytopathology,* 85, 1219-1224

Röhner et al. (2004), *Journal of Plant Diseases and Protection,* 111, 83-95

Slusarenko et al. (2008), *European Journal of Plant Pathology,* 121, 313-322

Stephan et al. (2005), *European Journal of Plant Pathology,* 112, 235-246

Tyler and Olsson (2006), *Chemosphere,* 65, 250-260

Widmer and Laurent (2006), *European Journal of Plant Pathology,* 115, 377-388

The invention claimed is:

1. A plant extract comprising at least one phenolic compound, wherein the plant extract is obtained according to a process comprising the steps of:

mixing a solvent with a solid fraction of carbonated sugar beet root juice obtained by carbonating sugar beet root juice produced from sugar beet root, wherein said solvent is ethanol or a combination of water and ethanol which comprises an amount of ethanol sufficient to extract said at least one phenolic compound into a supernatant;

allowing said mixture of said solvent and said solid fraction of said carbonated sugar beet root juice to settle, forming a supernatant and settled solids; and separating said supernatant from said settled solids, wherein said supernatant comprises the plant extract.

2. The plant extract according to claim 1, comprising p-hydroxybenzoic acid at a concentration of more than 5 μg/ml.

3. The plant extract according to claim 2, wherein said plant extract comprises p-hydroxybenzoic acid at a concentration of at least 10 μg/ml.

4. The plant extract according to claim 1, wherein allowing said mixture to settle comprises allowing said mixture to settle during an extraction time selected within an interval of from 30 minutes up to 24 hours.

5. The plant extract according to claim 4, wherein allowing said mixture to settle comprises allowing said mixture to settle during an extraction time selected within an interval of from 1 hour up to 6 hours.

6. The plant extract according to claim 1, wherein the process further comprises the steps of:

filtering said supernatant to remove suspended particles from said supernatant; and centrifuging said filtered supernatant to form said plant extract in liquid form.

7. The plant extract according to claim 1, wherein said solid fraction of said carbonated sugar beet root juice is obtained from a process comprising the steps of:

slicing sugar beet root;

producing sugar beet root juice from said sliced sugar beet root; and carbonating said sugar beet root juice to form said solid fraction of said carbonated sugar beet root juice.

8. The plant extract according to claim 7, wherein carbonating said sugar beet root juice comprises:

mixing said sugar beet root juice with a suspension of calcium hydroxide in water to form an alkaline sugar solution;

bubbling carbon dioxide through said alkaline sugar solution to precipitate said calcium hydroxide as calcium carbonate particles entrapping and absorbing impurities in said sugar beet root juice; and removing a liquid fraction to form said solid fraction of said carbonated sugar beet root juice.

9. The plant extract according to claim 1, further comprising:

Al at a concentration of 0.02-0.03 mg/l;

B at a concentration of 0.3-0.4 mg/l;

Ca at a concentration of 6-18 mg/ml;

Cu at a concentration of 0.05-0.11 mg/l;

Fe at a concentration of 0.10-0.18 mg/l;

K at a concentration of 34-68 mg/l;

Mg at a concentration of 0.33-1.1 mg/l;

Mn at a concentration of 0.03-0.06 mg/l;

Mo at a concentration of 0.0008-0.0017 mg/l;

Na at a concentration of 3.4-6.5 mg/ml;

S at a concentration of 4.4-4.8 mg/l;

Se at a concentration of 0.8-1 mg/l; and

Zn at a concentration of 0.05-0.15 mg/l of said plant extract in undiluted form.

10. A composition comprising a plant extract according to claim 1 and at least one plant signaling agent and/or fungicide and/or bactericide.

11. The composition according to claim 10, formulated as a foliar spray.

12. A method of inducing resistance to biotic stress in a plant comprising applying a plant extract according to claim 1 to said plant.

13. The method according to claim 12, wherein said biotic stress is caused by a *Phytophthora* oomycete.

14. The method according to claim 13, wherein said biotic stress is caused by *Phytophthora infestans*.

15. The method according to claim 12, wherein said plant belongs to the Solanaceae family.

16. The method according to claim 15, wherein said plant is *Solanum tuberosum*.

17. A method of treating or inhibiting late blight disease in a plant comprising applying a plant extract according to claim 1 to said plant.

18. The method according to claim 17, wherein said plant belongs to the Solanaceae family.

19. The method according to claim 18, wherein said plant is *Solanum tuberosum*.

20. A method of manufacturing a plant extract comprising at least one phenolic compound, wherein said method comprises the steps of:
   mixing a solvent with a solid fraction of carbonated sugar beet root juice obtained by carbonating sugar beet root juice produced from sugar beet root, wherein said solvent is ethanol or a combination of water and ethanol which comprises an amount of ethanol sufficient to extract said at least one phenolic compound into a supernatant;
   allowing said mixture of said solvent and said solid fraction of said carbonated sugar beet root juice to settle, forming a supernatant and settled solids; and
   separating said supernatant from said settled solids, wherein said supernatant comprises the plant extract.

21. The method according to claim 20, wherein producing said plant extract comprises the steps of:
   filtering said supernatant to remove suspended particles from said supernatant;
   centrifuging said filtered supernatant to form said plant extract in liquid form; and
   optionally diluting said centrifuged filtered supernatant to form said plant extract in liquid form.

22. The method according to claim 20, wherein the solid fraction of carbonated sugar beet root juice is obtained by:
   slicing a sugar beet root;
   producing sugar beet root juice from said sliced sugar beet root; and
   carbonating said sugar beet root juice to form said solid fraction of said carbonated sugar beet root juice.

23. The method according to claim 22, wherein carbonating said sugar beet root juice comprises:
   mixing said sugar beet root juice with a suspension of calcium hydroxide in water to form an alkaline sugar solution;
   bubbling carbon dioxide through said alkaline sugar solution to precipitate said calcium hydroxide as calcium carbonate particles entrapping and absorbing impurities in said sugar beet root juice; and
   removing a liquid fraction to form said solid fraction of said carbonated sugar beet root juice.

24. The method according to claim 20, wherein allowing said mixture to settle comprises allowing said mixture to settle forming said supernatant and said settled solids during an extraction time selected within an interval of from 30 minutes up to 24 hours.

25. The method according to claim 24, wherein allowing said mixture to settle comprises allowing said mixture to settle forming said supernatant and said settled solids during an extraction time selected within an interval of from 1 hour up to 6 hours.

26. The method according to claim 25, wherein allowing said mixture to settle comprises allowing said mixture to settle forming said supernatant and said settled solids during an extraction time selected within an interval of from 1 hour up to 4 hours.

27. The plant extract according to claim 5, wherein allowing said mixture to settle comprises allowing said mixture to settle during an extraction time selected within an interval of from 1 hour up to 4 hours.

* * * * *